United States Patent
Friedman

(12) 
(10) Patent No.: US 6,254,825 B1
(45) Date of Patent: Jul. 3, 2001

(54) ANTIFOAM COMPOSITIONS INCLUDING LECITHIN AND USES THEREOF

(75) Inventor: Robert S. Friedman, Los Angeles, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/283,529

(22) Filed: Apr. 1, 1999

(51) Int. Cl.[7] .......................... A61M 1/14; A61M 37/00; B01D 37/02; B01D 47/00
(52) U.S. Cl. ......................... 422/44; 422/45; 604/4.01; 604/6.15; 604/403; 210/193; 210/750; 261/2; 96/156
(58) Field of Search .................. 604/4–6, 4.01, 604/6.14, 6.15, 403, 405, 251, 252, 255; 422/44–48; 261/2, 3, 5–6; 96/4, 6, 155, 176, 179–81, 219, 234–35, 240, 290, 296, 298–99; 210/750, 193; 554/500.1, 500.27, 80

(56) References Cited

U.S. PATENT DOCUMENTS

| 4,188,412 | 2/1980 | Sejpal . |
| 4,609,490 | 9/1986 | Itoh et al. . |
| 4,704,203 | 11/1987 | Reed . |
| 5,039,486 | 8/1991 | Gordon . |
| 5,110,549 | 5/1992 | Gordon . |
| 5,152,964 | 10/1992 | Leonard . |
| 5,167,921 | 12/1992 | Gordon . |
| 5,192,439 | 3/1993 | Roth et al. . |
| 5,211,913 | * 5/1993 | Hagiwara et al. ..................... 422/44 |
| 5,242,384 | 9/1993 | Robinson et al. . |
| 5,244,930 | 9/1993 | Trudell et al. . |
| 5,304,164 | 4/1994 | Lindsay . |
| 5,411,705 | * 5/1995 | Thor et al. ............................ 422/45 |
| 5,458,905 | 10/1995 | Heagle . |
| 5,568,973 | * 10/1996 | Gorab .................................. 366/129 |
| 5,824,359 | 10/1998 | Khan et al. . |
| 5,846,454 | * 12/1998 | Koczo et al. ........................ 252/358 |
| 5,990,181 | * 11/1999 | Spyropoulos et al. ............... 516/118 |

FOREIGN PATENT DOCUMENTS

| 0450605 | 10/1991 | (EP) . |
| 0630656 | 12/1994 | (EP) . |
| 0774285 | 5/1997 | (EP) . |
| 9221387 | 12/1992 | (WO) . |

OTHER PUBLICATIONS

Patent Abstacts of Japan, Yoshida Fumiko, defoaming agent for food, Nov. 29, 1994.
Database WPI, Fujisawa Pharm Co LTD, defoaming agent, Apr. 16, 1987.

* cited by examiner

Primary Examiner—Angela D. Sykes
Assistant Examiner—Patricia Bianco
(74) Attorney, Agent, or Firm—Mueting, Paasch & Gebhardt, P.A.

(57) ABSTRACT

A composition including lecithin which is useful for defoaming liquids, such as blood. In one aspect of the invention the composition includes inorganic particles. In another aspect of the invention the composition includes a silicone.

14 Claims, 2 Drawing Sheets

ANTIFOAM COMPOSITIONS INCLUDING LECITHIN AND USES THEREOF

BACKGROUND

From the first operation to repair a heart in 1891 until the early 1950's, heart surgeons were limited by the problem of trying to work on the heart while it was still beating. The heart's constant motion, and the presence of blood that obscured the surgeon's view, made repairing heart defects a surgical challenge. Surgeons had to work quickly and there was always a danger of disrupting blood circulation to vital organs. The solution to this problem came in the late 1950's with the development of the first oxygenator.

The veins return deoxygenated blood to the heart's right atrium. From the right atrium, blood is pumped to the right ventricle, then through the pulmonary artery to the lungs. The lung oxygenates the blood while removing carbon dioxide as it passes through the lung's alveolar capillary network. Oxygenated blood is then returned to the left atrium by way of the pulmonary veins. Blood is then pumped through the mitral valve into the left ventricle and pumped back into the body's circulatory system. Cells are replenished with oxygen and carbon dioxide is taken up by the blood as the blood passes through the body's capillary system. After this gaseous exchange is accomplished, the blood is returned to the heart and the cycle is repeated.

During cardiopulmonary by-pass (CPB) surgery, for example, venous blood is taken from the patient's circulation by means of a cannula placed in the vena cava. The blood "by-passes" the heart and lungs and enters what is referred to as the "extracorporeal circuit" or literally a circuit "outside the body." Oxygenation of the patient's blood takes place in an oxygenator much in the same way as it does in the natural process. After the blood is oxygenated and temperature regulated, it is returned to the patient's arterial circulation through a cannula so that the patient's body may utilize the oxygenated blood.

Early blood oxygenators were called "bubblers" because they bubbled air up through a column of blood, diffusing oxygen into the blood and carbon dioxide out. The problem was that this bubbling action created foam which not only was damaging to the blood, but also rendered this portion useless to the patient.

A defoaming sponge was employed to break down the bubbles of foam back into usable liquid blood. However, the raw sponge by itself was ineffective without a surface agent to lower the surface tension of the blood foam. Silicone Antifoam "A" by Dow Corning was adopted throughout the industry as the defoaming agent of choice. It is comprised of silicone oil and approximately 4.5% silica particles (approximately 5 micrometer (i.e., micron) in diameter). Another development was the use of blood reservoirs to process blood suctioned (scavenged) from the patient during surgery. Antifoam A was used to coat defoaming sponges used in blood reservoirs here as well.

The silicones used in typical silicone antifoams are hydrophobic. Therefore, these compounds are typically dissolved in organic solvents in order to prepare an antifoam solution, which can be applied to a surface to reduce foaming of liquids contacting the surface. The primary solvents that have been used heretofore are chlorofluorocarbons (CFCs) because they are nonflammable and evaporate quickly. Unfortunately, because of recent concerns that CFCs affect the earth's protective ozone layer, the production and use of CFCs will cease in the near future. Thus, there is a need in the art for alternative defoaming compositions having fewer if any detrimental side effects to the individual and the environment.

SUMMARY OF THE INVENTION

The present invention provides compositions comprising (and preferably, consisting essentially of) lecithin, such as soy lecithin, and preferably inorganic particles, such as silica particles, and optionally a diluting agent. Such compositions are particularly suitable as defoaming (i.e., antifoaming) compositions. Typically, such compositions are coated on a surface of an article, such as a surface in a cardiotomy reservoir. Alternatively, however, compositions of the present invention can be added directly to a liquid prone to foaming.

Preferably, compositions of the present invention also include a diluting agent, such as water or alcohol. Optionally, compositions of the present invention can include a silicone. In preferred compositions, the ratio of diluting agent to lecithin is at least about 7:1 parts diluting agent to lecithin, and the amount of inorganic particles is preferably about 2 weight-% to about 20 weight-% inorganic particles, based on the weight of the lecithin in the composition.

Surfaces on which compositions of the present invention can be coated for desired effect include surfaces of devices through which liquids prone to foaming pass or are stored, for example. This includes portions of extracorporeal circuits, particularly cardiotomy reservoirs. Alternatively, instead of being directly coated on a surface of a device through which a liquid passes or is stored, compositions of the present invention can be coated on articles that are placed in such devices, such as defoaming sponges, which are often open cell sponges, for example.

The present invention also provides a method of reducing foaming in a liquid prone to foaming. The method includes contacting the liquid prone to foaming with an antifoam composition comprising lecithin and inorganic particles, wherein the amount of foam present in the liquid combined with the antifoam composition is decreased relative to the same liquid under the same conditions without the antifoam composition. Such liquids prone to foaming include, for example, blood, milk, beer, and soda.

The composition can be added to the liquid prone to foaming or be coated on a surface with which the liquid comes in contact. Such methods are typically performed during surgery, such as cardiopulmonary surgery, orthopedic surgery, and thoracic surgery, and are used to reduce foaming in blood. Preferably, at least one characteristic of foaming in a liquid, such as blood, is reduced. That at least one characteristic is selected from the group of wicking, streaming, spotting, scud formation, and backup/overflow.

Significantly, by reducing foaming in blood, trauma to the blood can be reduced. Thus, the present invention provides a method of reducing trauma to blood in an extracorporeal circuit comprising combining blood with a composition comprising lecithin and inorganic particles. This combining step typically occurs by coating one or more surfaces of the extracorporeal circuit or an article therein, such as a sponge, with which the blood comes in contact with the antifoam composition.

Definitions

A "cardiotomy reservoir" can be part of a device used to store blood that has been removed from a patient until the blood is returned to the patient. The "cardiotomy reservoir" includes a surface, e.g., a defoaming sponge, that is used to decrease the amount of foam in the blood removed from the patient, and the reservoir into which blood flows immediately following treatment to decrease foaming. The device that of which the "cardiotomy reservoir" forms a part is referred to as an "extracorporeal circuit." Extracorporeal circuits include, for example, oxygenators, reservoirs, filters, tubing, connectors, valves, sensors, and devices used to scavenge blood from a patient during surgery.

"Foam" refers to a gas dispersed in a liquid such that bubbles are formed. "Defoam," "defoamed," and "defoaming" refer to decreasing the amount of foam in a liquid by decreasing the amount of gas dispersed in the liquid. The amount of foam present in a liquid can be determined by, for instance, measuring the volume of foam present on top of the liquid containing the foam.

"Defoaming sponge" refers to a surface that can be used to decrease foaming of a liquid. Typically, a liquid prone to foaming flows through the defoaming sponge and causes a decrease in the amount of foam in the liquid. A "defoaming sponge" is typically an open cell sponge.

A "liquid prone to foaming" refers to a liquid that, when subjected to certain conditions including, for instance, oxygenation or mixing, forms a foam.

DETAILED DESCRIPTION OF THE PREFERRED EMBODIMENTS

Figure 1:
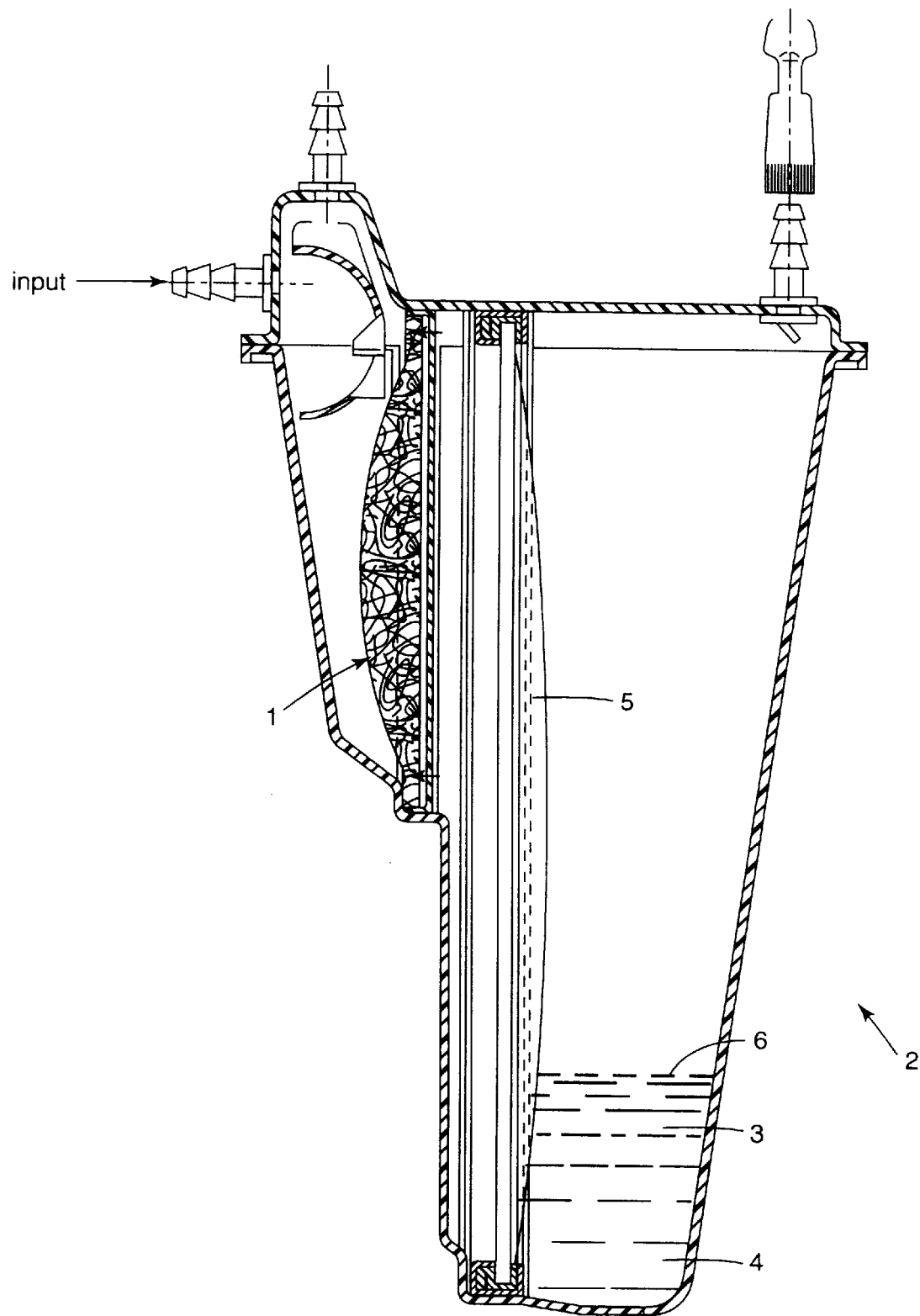
FIG. 1. A cardiotomy reservoir.

The present invention is directed to a composition including lecithin. In one aspect of the invention the composition includes inorganic particles. In another aspect of the invention the composition includes a silicone. The silicone can be present in a silicone antifoam, which is a mixture of silicone oil and silica particles. The composition can further include a diluting agent. The compositions (optionally referred to herein as antifoam agents or antifoam compositions) can be used to coat surfaces that contact liquids prone to foaming or added directly to liquids prone to foaming. Preferably, the surface is in an extracorporeal circuit, more preferably in a cardiotomy reservoir, most preferably a defoaming sponge in a cardiotomy reservoir. Preferably, the liquid prone to foaming is blood. Preferably, the blood is present in an extracorporeal circuit during, for example, cardiovascular surgery, or orthopedic surgery, or thoracic surgery. Alternatively, the blood is suctioned from a patient during surgery. Typically, blood removed from a patient during surgery is oxygenated and/or stored in a reservoir.

Some aspects of the invention are beneficial as they have fewer detrimental effects to the environment. In particular, certain preferred compositions of the present invention are water based and do not require the use of environmentally harmful CFC solvents. Moreover, some of the compositions of the present invention reduce the detrimental side effects that may occur from using silicones as defoaming agents. Thus, certain preferred embodiments do not include a silicone.

It was originally hypothesized that the levels of lecithin needed to decrease foaming would be identical to the levels of silicone antifoam. Surprisingly, it was unexpectedly found that less lecithin was needed to function substantially the same as the silicone. This is an advantage, as a liquid prone to foaming is exposed to a lesser amount of a composition of the present invention to effectively decrease foaming. Moreover, it was not expected that silica particles would play such a major role in the compositions that do not include silicone. It was originally hypothesized that all that need be done to defoam blood is to reduce its surface tension by introduction of lecithin. However, the bubbles that form foamed blood are very tenacious, being surrounded with a layer of protein. Apparently, the silica particles provide, through abrasive interaction with the blood bubble, the introduction of the surface tension reducing agent needed to pop the bubble. Typically, without the inorganic particles, the agent cannot effectively penetrate the bubble surface.

Lecithin is a naturally occurring substance that can be obtained from, for example, soybean or egg. Lecithins are typically mixtures of diglycerides of fatty acids linked to the choline ester of phosphoric acid, and are classed as phosphoglycerides or phosphatides (phospholipids). Lecithin can contain differing amounts of other compounds depending on the method of isolation. Typically, commercial lecithin is a mixture of acetone-insoluble phosphatides. Preferably, the lecithin is obtained from seeds including soybean and corn, most preferably soybean, using methods well known in the art. Lecithin obtained from soybean is referred to herein as soy lecithin. Although lecithin can also be derived from egg yolk, the pharmaceutical industry has focused on soy based lecithin because of its lower risk of disease. For instance, soy lecithin has been used extensively in the intravenous (I.V.) feeding industry.

Lecithin, in its various mixtures, is sold under such commercial trade names as Central Soya CENTROMIX E lecithin, Product Code #6230, available from Central Soya (Fort Wayne, Ind.), and PHOSPHOLIPON 90H lecithin, (American Lecithin Co., Oxford, Conn.). Preferably, Centromix E or PHOSPHOLIPON 90H lecithin is used in compositions of the present invention. Preferably, in applications requiring high purity (e.g., intravenous applications or blood defoaming), PHOSPHOLIPON 90H lecithin is used. Alternatively, CENTROMIX E lecithin can be used in applications not requiring high purity. The composition can be prepared by mixing lecithin and inorganic particles together, optionally with a diluting agent. Various combinations of lecithins, inorganic particles, and diluting agents can be used if desired. Preferably, for such embodiments, the compositions include at least about 7 weight-% lecithin, more preferably at least about 10 weight-% lecithin, and most preferably at least about 12 weight-% lecithin, based on the total weight of the lecithin and diluting agent. Preferably, for such embodiments containing lecithin and silica (without silicone) the composition contains no more than about 20 weight-% of lecithin, based on the total weight of the lecithin and diluting agent.

The particles useful in the present invention include inorganic particles. The particles are typically in the form of an amorphous sol or an amorphous powder. The use of a powder can result in an intractable mass. However, with the proper mixing equipment (for instance a shear mixer) and care in adding ingredients (e.g., adding ingredients slowly, using heat as described herein to encourage solubility, or first mixing particles into the diluting agent then adding the lecithin), problems with having a mass are avoided. Powders and sols useful in the present compositions can be prepared by methods well known in the art. As used herein, "sol" refers to a colloidal dispersion of substantially non-aggregated, inorganic particles in a liquid medium. Colloidal silicas dispersed as sols in aqueous solutions are available commercially under such trade names as LUDOX (E.I. DuPont de Nemours and Co., Wilmington, Del.), NYACOL (Nyacol Co., Ashland, Mass.), and NALXO (Nalco Chemical Co., Oak Brook, Ill.). Nonaqueous silica sols (also called silica organosols) are also commercially available under the trade names NALCO 1057 (a silica sol in 2-propoxyethanol, Nalco Chemical Co.), and MA-ST, IP-ST, and EG-ST (Nissan Chemical Ind., Tokyo, Japan). Amorphous silicas are commercially available under such trade names as SYLOID 244 (WR Grace Davison Chemical Division, Baltimore, Md.). Preferably, the inorganic particle is silica, most preferably, SYLOID 244.

In addition to silica, other inorganic particles may be used, including, but not limited to, alumina, titania, zirconia, ceria, and antimony oxide, all of which are available commercially as sols from suppliers such as Nyacol Co., Ashland, Mass., and Nalco Chemical Co., Oak Brook, Ill. Various combinations of inorganic particles can be used if desired.

The inorganic particles preferably have an average particle diameter of at least about 4 microns to about 6 microns, and more preferably, about 5 microns. In applications where the composition contacts a liquid prone to foaming that is to be introduced into a patient (e.g., blood, intravenous solution) the inorganic particles preferably have an average particle diameter of no greater than about 7 microns. In other applications it is expected that there is no upper limit on the inorganic particle. The approximate particle size distribution may typically be a minimum of 99.95% on a US Standard screen through 325 mesh. Average particle size can be measured using transmission electron microscopy to count the number of particles of a given diameter. Preferably, compositions of the present invention include at least about 2 weight-% inorganic particles, more preferably at least about 3 weight-% inorganic particles, and most preferably at least about 5 weight-% inorganic particles, based on the weight of the lecithin used in the composition. Preferably, the composition contains no more than about 20 weight-% inorganic particles, based on the total weight of the lecithin.

If desired, compositions of the present invention include a diluting agent. Useful diluting agents include water, alcohols, and chlorinated hydrocarbons (CFCs). The type of diluting agent useful in a composition depends on the composition to be defoamed. When the liquid prone to foaming is used in the food industry, preferably the diluting agent is water. When the liquid prone to foaming is present in an extracorporeal circuit, preferably the diluting agent is an alcohol, more preferably isopropanol or ethanol. Alcohols have the added benefit of readily evaporating. Preferably, the diluting agent is water, an alcohol, or mixtures thereof. The ratio of diluting agent to lecithin can vary depending on the application. For example, for blood, a ratio of 12:1 (parts diluting agent to lecithin) is particularly desirable. For other liquids, other concentrations may be desired, which can be determined by one of skill in the art.

As stated above, a silicone can be included in the compositions of the present invention. Typically, a silicone is added as a part of a silicone antifoam. Silicone antifoams useful in the present invention include Silicone Antifoam-A (Dow Corning, Midland, Mich.) and silicone antifoams made by GE Silicones (Waterford, N.Y.) and Union Carbide Corp., (Danbury, Conn.). Preferably, Silicone Antifoam-A is used. The composition can be prepared by mixing lecithin, silicone antifoam, and a diluting agent. Useful diluting agents include water, alcohols, and chlorinated hydrocarbons (CFCs). The type of diluting agent useful in a composition depends on the composition to be defoamed. When the liquid prone to foaming is used in the food industry, preferably the diluting agent is water. When the liquid prone to foaming is present in an extracorporeal circuit, preferably the diluting agent is an alcohol, more preferably isopropanol or ethanol. Preferably, such embodiments include at least about 20 weight-% lecithin, more preferably at least about 25 weight-% lecithin, most preferably at least about 30 weight-% lecithin, where the weight-% lecithin is calculated based on the weight of silicone antifoam present in the composition, not on the weight of the total composition. Preferably, such compositions that include a silicone antifoam contain no more than about 50 weight-% lecithin. Preferably, the ratio of diluting agent to silicone antifoam is at least about 10 parts to 1 part, and more preferably at least about 16 parts to 1 part. Preferably, the composition contains no more than about 20 parts to 1 part diluting agent to silicone antifoam.

Methods can be used to produce a homogenous mixture of lecithin and the other components of the present invention, preferably, silica particles, and optionally a diluting agent. A homogenous mixture can be obtained by using a homogenizer or a shear mixer. Typically, if a diluting agent is used, the composition is preferably prepared by mixing a diluting agent with soy lecithin and then adding inorganic particles. Without intending to be limiting, mixing can be done at, for instance, 2,500 RPM. Optionally, the temperature of the composition components can be increased before mixing and/or during mixing to aid the mixing process. Preferably, the components of the composition are heated separately before being combined and mixed. Preferably, the components are heated, either individually or in a mixture, to about 60° C., more preferably to about 75° C., most preferably to about 90° C.

Compositions of the present invention can be used in methods to reduce foaming in a liquid prone to foaming. For example, the composition can be added directly to the liquid, or the composition can be used to coat a surface that the liquid will contact. For instance, the composition can be added directly to liquids during food preparation, such as beer, milk, or soda, or directly to medicines, such as intravenous feeding products, or to liquids used in sewage and wastewater treatment plants.

Alternatively and preferably, a composition of the present invention is used to coat a surface that the liquid will contact. For instance, the compositions can be applied to a surface that is part of an apparatus, e.g., an extracorporeal circuit, that comes in contact with a liquid prone to foaming. Such surfaces also include an open cell sponge present in a cardiotomy reservoir, semi-permeable membranes including, for instance, an asymmetric microporous hollow fiber membrane, and simple substrates including, for example, the tubes of an extracorporeal circuit. Preferably, the surface is a part of a sponge, such as an open cell sponge. For an article such as an open cell sponge, a composition of the present invention can be coated on an external surface or impregnated into the body such that internal surfaces are coated.

An open cell sponge useful in the invention is typically made up of a plastic polymer containing pockets of air or gas introduced before the plastic has cured. Open cell sponges are produced using methods known to the art. The open cell sponge can be made of polyurethane, polyester, or polyethylene, and preferably, polyurethane.

Surfaces can be coated with the compositions by spraying or by atomizing. Spraying the composition onto a surface can be accomplished by loading the composition into a pressure pot having a pressure set at about 20 psig to about 60 psig (depending on the size of the sponge to be treated) and forced through a nozzle (preferably with 0.028 inch fluid orifice and 0.050 inch air orifice) (part number 2850SS, available from Spray Manufacturing Systems Co., Laguna Hills, Calif.). Typically, the composition is not diluted when it is to be sprayed, except in high purity applications where the lecithin is dispersed in water or alcohol prior to usage.

Alternatively, the surface can be coated by dipping the surface into the composition, or when being applied to the tubing of an extracorporeal circuit, the circuit can be flushed with the composition. When the composition is to be applied to a surface in a manner other than spraying, the composition is typically diluted with a diluting agent. Typically the surface is allowed to dry before use. The surface can be allowed to dry at room temperature. Alternatively, the surface can be allowed to dry in an oven for about 4 hours to about 12 hours. Preferably, the temperature of the oven is about 50° C. to about 70° C. In general, conditions for drying can vary depending on, for example, the substrate and/or the mixture concentration.

If necessary, the coated surface can be sterilized. Sterilization methods include gamma irradiation by Cobalt 60, irradiation by e-beam, and by ethylene oxide.

Typically, the performance of a coated surface can be evaluated in a Defoaming Performance Test. This test compares the behavior of coated and uncoated surfaces, or surfaces coated with different compositions. Preferably, the surface is a defoaming sponge. A liquid prone to foaming, preferably blood, entering an extracorporeal circuit is mixed with an equal volume flow rate of air to create a foamed liquid. The air is either introduced with positive pressure or a vacuum is connected to the extracorporeal circuit to draw the air into the liquid and control the blood flow. Preferably, a vacuum is connected to the extracorporeal circuit to draw the air into the liquid. The ability of the coated surface is measured by how well it reduces the foam to useable liquid.

Referring to FIG. 1, performance of an antifoam composition on a defoaming sponge 1 can be assessed by visual observation of several parameters, which are described by referencing the cardiotomy reservoir 2 that includes a defoamed liquid 3 present in a receptacle 4. Compositions of the present invention provide improvement in at least one, and preferably, more than one, of the following parameters: i) spotting, i.e., the localized absorption of liquid on the filter assembly 5 (typically, containing filtration media such as felt) above the defoamed liquid level 6; ii) wicking, i.e, the absorption of liquid on the filter assembly 5 above the defoamed liquid level 6; iii) streaming, i.e., stream of liquid breaking through the filter 5 above the defoamed liquid level 6; iv) scud formation, i.e., the formation of microbubbles on the defoamed liquid level 6 of the defoamed liquid 3 present in the portion 4 of the cardiotomy reservoir 2, i.e., downstream of the defoaming sponge 1 and filter assembly 5; and v) backup/overflow, e.g., the flow of liquid and/or foam directly over or around the filter assembly 5 and into the reservoir 4 of the cardiotomy reservoir 2. Backup/overflow is an indication of device failure. Another indication of failure is macroemboli flowing over the top of the filter assembly 5 and into the blood reservoir.

Typically, the performance of a coated surface can also be evaluated in a Blood Trauma Test. Since foaming damages blood, a blood trauma test can be used to assess the benefit provided by antifoam compositions of the present invention. Typically, blood trauma is measured in at least one of three ways: (1) assessing breakage of red blood cells by measuring generated plasma hemoglobin; (2) platelet depletion over the time of the assay relative to the number of platelets present at the beginning of the assay; and (3) white blood cell depletion over the time of the assay relative to the number of white blood cells present at the beginning of the assay. Compositions of the present invention provide improvement in at least one of these parameters, and preferably, in more than one of these parameters.

The present invention is illustrated by the following examples. It is to be understood that the particular examples, materials, amounts, and procedures are to be interpreted broadly in accordance with the scope and spirit of the invention as set forth herein.

Example 1

Coating of INTERSEPT 1351 Cardiotomy Reservoirs with a Composition Comprising Soy Lecithin, Water, and Silica Particles, the Lydall Aqueous Process, or with Silicone Antifoam A.

The composition was prepared by mixing ten parts water with one part soy lecithin (Centromix E) by weight. The two components were heated to 60° C., then mixed together by shear mixing for 10 minutes at as high a speed as possible without sucking air into the emulsion. Approximately 4% to 5% of 5 micron silica particles (Syloid 244 FP) were added. Two INTERSEPT defoaming sponges from INTERSEPT 1351 cardiotomy reservoirs (Medtronic, Inc., Anaheim, Calif.) were dipped into the lecithin solution and allowed to dry, and then assembled into the cardiotomy reservoir. These reservoirs were labeled T3 and T4.

Two INTERSEPT defoaming sponges were prepared using the Lydall Aqueous Process by a proprietary process (Lydall Westex, Inc., Hamptonville, N.C.). These reservoirs were labeled T1 and T2.

Six cardiotomy reservoirs were used as production controls. A production control contains an INTERSEPT defoaming sponge coated with Silicone Antifoam A. The Silicone Antifoam A was applied using Freon (10 parts Freon to 1 part antifoam) to disperse it, followed by dipping of the sponges and volatilization of the Freon. These reservoirs were labeled C1–C6.

Evaluation of Blood Defoaming Characteristics.

Figure 2:
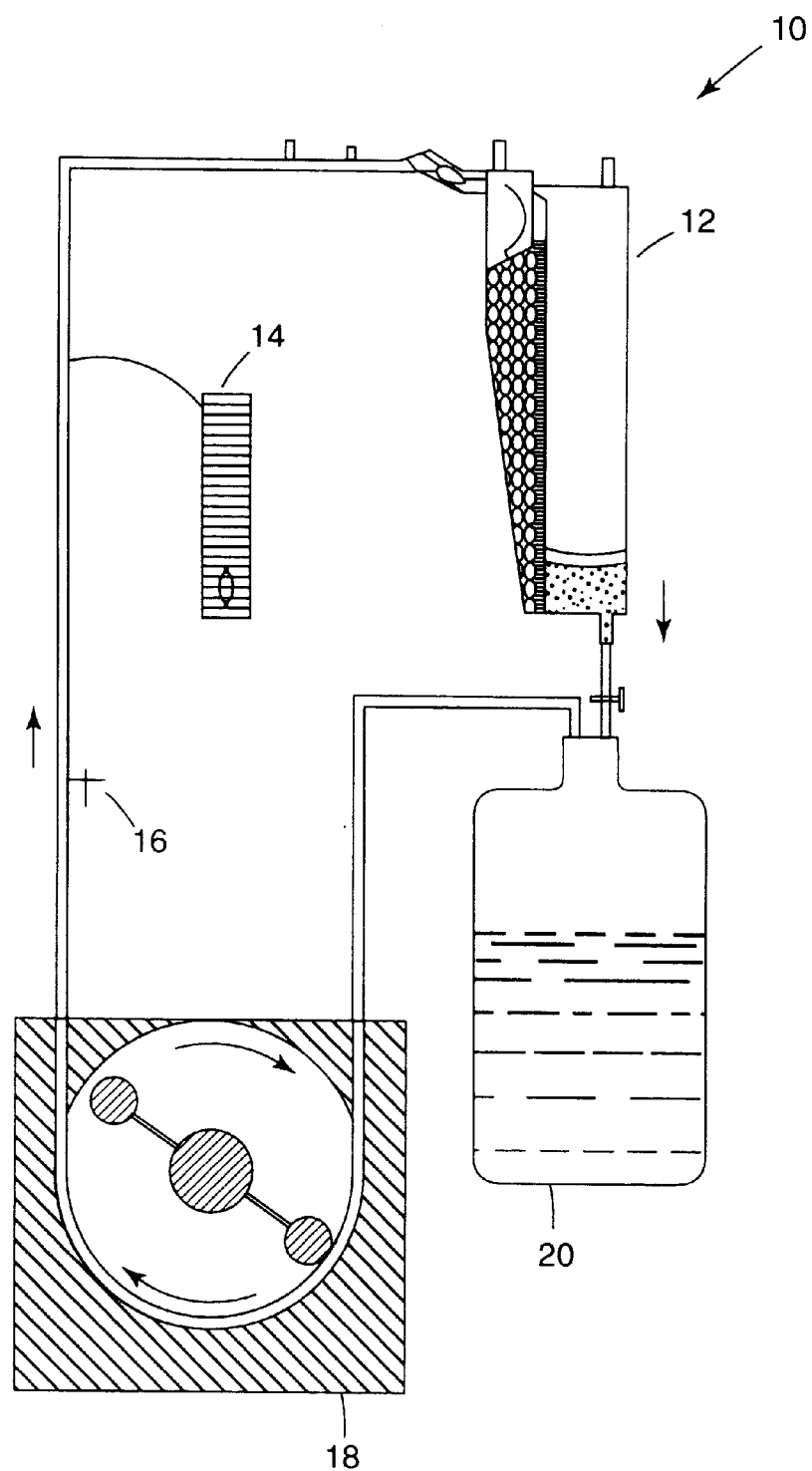
FIG. 2. An extracorporeal circuit.

A Defoaming Performance Test was conducted in vitro comparing cardiotomy reservoirs containing surfaces treated with the soy lecithin-silica particle composition with cardiotomy reservoirs containing surfaces treated with either the Lydall process composition or Silicone Antifoam A. The test was run using an extracoporeal circuit schematically depicted in FIG. 2 that included a cardiotomy reservoir schematically depicted in FIG. 1. The circuit 10 shown in FIG. 2 includes a cardiotomy reservoir 12 (of the type shown in FIG. 1), a gas flow meter 14, a sample port 16, a roller pump 18, and a reservoir 20. The test was run for 6 hours. This blood flow was combined with introduction of air bubbles in the ratio of 1:1 (blood flow to air flow). Foam was thus generated and a relative comparison was made.

After assembly of the cardiotomy reservoirs, fresh anticoagulated bovine blood was filtered and diluted to a hemoglobin of $9.0 \pm 0.3$ g/dl. Two liters of blood were added to the device reservoir 1 and the test was begun. Defoaming testing was performed at Qb:Qg=2:1 LPM. This refers to the ratio of blood flow rate into the device in liters per minute (LPM) to the rate of gas introduced in liters per minute. Thus there were 2 liters per minute of blood entering the device for every 1 liter of gas introduced to create foam. Defoaming characteristics were evaluated at 30 minute intervals, for six hours, while maintaining the cardiotomy reservoir fluid level at 200 ml. Performance of treated and control reservoirs in the Defoaming Performance Test was assessed by visual observation of wicking, streaming, spotting, scud formation, and backup/overflow.

All four test samples (T1, T2, T3, and T4) exhibited scud within the first thirty minutes (T2 and T3 at 15 minutes; T1 and T4 at 30 minutes). Four of the six controls exhibited scud at thirty minutes, one at sixty minutes and one did not during the 6 hour recirculation period. Both Centromix E samples (T3 and T4) failed during the six hour period (one at 120 minutes and one at 210 minutes), while two of the controls failed (one at 210 minutes and one at 240 minutes) and neither of the Lydall samples failed. One each of the test samples exhibited spotting (T3 at 30 minutes; T1 at 330 minutes), while none of the controls did. One of the Centromix E samples exhibited streaming (T3 at 30 minutes) while none of the Lydall samples or the controls did.

Summary—The Lydall product was inconsistent where T1 performed well compared to controls, while T2 did not. T3 and T4 were more consistent, but did not exhibit a high enough defoaming action to be comparable to controls.

Example 2
Coating of INTERSEPT 1351 Cardiotomy Reservoirs with a Composition Comprising Soy Lecithin, Water, and Standard Silicone Antifoam A.

The following three compositions (Table 1) were produced by heating each ingredient to 65° C. before combining. The 300 ml volume of water was combined with the Centromix E/Silicone Antifoam A mixture and mixed by shear mixing for 10 minutes at as high a speed as possible without sucking air into the emulsion. The remaining volume of water was then added and mixed. Seven INTERSEPT defoaming sponges were dipped into each composition and dried. After assembly, the cardiotomy reservoirs were sterilized by gamma irradiation. The results for the production controls tested in Example 1 were used in evaluating the reservoirs in this Example.

TABLE 1

Compositions including Silicone Antifoam A.

| Group | Centromix E (g) | Silicone (g) | Water (ml) |
|---|---|---|---|
| 1. | 20 | 100 | 300 + 700 |
| 2. | 25 | 100 | 300 + 700 |
| 3. | 30 | 100 | 300 + 1300 |

Evaluation of Blood Trauma and Defoaming Characteristics.

The INTERSEPT cardiotomy reservoirs were evaluated in vitro to determine the effect of various amounts of Centromix E emulsifier on blood trauma characteristics and defoamer performance. All test samples were comparatively evaluated against production controls. Three reservoirs from each of group 1, group 2, and group 3 and three production controls were tested for blood trauma. Four reservoirs from each of group 1, group 2, and group 3 and four production controls were evaluated for defoaming.

The cardiotomy reservoirs were tested for blood trauma at Qb=Qg=1 LPM, room temperature, 11.5±0.3 g/dl hemoglobin. Defoaming testing was performed at Qb=Qg=1 LPM on two each of the test samples and two of the controls, and at Qb=2 LPM; Qg=1 LPM on two each of the test samples and two of the controls.

Blood Trauma

Mean values for cardiotomy reservoirs of groups 1 and 3 were either not significantly different or significantly lower ($p<0.05$) than those of the controls, while mean six hour generated plasma hemoglobin for cardiotomy reservoirs of group 2 was significantly higher (35.3±6.3 mg/dl vs. 23.4±2.4 mg/dl, $p<0.05$) than that of the controls.

Defoaming

All test samples did not exhibit wicking, streaming, spotting or scud at Qg=Qb=1 LPM, while all six of the production controls exhibited wicking by 210 minutes into the test. By the end of the six hour recirculation period, the test cardiotomy reservoirs had lower prefilter backup (group 1=500 ml, group 2=600 ml, group 3=500 ml, mean values) than the controls (1200 ml, mean value).

At the Qb=2 LPM; Qg=1 LPB portion of the defoaming, four of the six controls exhibited scud earlier than the test samples. Controls exhibited scud at 30 minutes while one test unit in group 2 held out until 90 minutes, and one unit in each of groups 1 and 3 held out until 150 minutes. Two of the controls failed during the six hour recirculation period (one at 210 minutes and one at 240 minutes), while none of the test samples failed. Three of the test units exhibited spotting (one from group 3 at 150 minutes, one from group 1 at 180 and a second one from group 1 at 270 minutes) while none of the controls did. One of the test samples exhibited streaming before the controls (one from group 1 at 180 minutes compared to three controls at 210 minutes). By the end of the six hour recirculation period, the test samples had significantly lower prefilter backup than the controls.

Summary—For blood trauma: A) General Plasma Hemoglobin for Group 1 was comparable to controls; Group 2 comparable thru 4 hours, then slightly higher at 6 hours; Group 3 comparable. B) Platelet depletion for Group 1 was significantly better than controls; Group 2 even more significantly better than controls; Group 3 same as group 2. C) White blood cell depletion: All groups comparable to controls. For defoaming all test units were significantly better than controls.

The complete disclosures of all patents, patent applications, and publications that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A cardiotomy reservoir comprising a surface coated with a non-silicone composition comprising lecithin and inorganic particles.

2. The cardiotomy reservoir of claim 1 wherein the composition further comprises a diluting agent.

3. The cardiotomy reservoir of claim 2 wherein the diluting agent is selected from the group of water and alcohol.

4. The cardiotomy reservoir of claim 2 wherein the ratio of diluting agent to lecithin is at least about 7:1.

5. The cardiotomy reservoir of claim 1 wherein the lecithin is soy lecithin.

6. The cardiotomy reservoir of claim 1 wherein the inorganic particles are silica particles.

7. The cardiotomy reservoir of claim 1 wherein the surface on which is coated the composition forms a part of an open cell sponge.

8. The cardiotomy reservoir of claim 1 which is a part of an extracorporeal circuit.

9. A device comprising a non-silicone antifoam composition comprising lecithin and inorganic particles.

10. The device of claim 9 which forms a part of an extracorporeal circuit.

11. The device of claim 9 comprising a surface on which is coated the antifoam composition.

12. The device of claim 9, wherein the device is a fluid handling device.

13. The device of claim 9, wherein the device is a blood handling device.

14. The device of claim 9, wherein the device is a blood reservoir.

* * * * *